US011198669B2

(12) United States Patent
Wu et al.

(10) Patent No.: US 11,198,669 B2
(45) Date of Patent: Dec. 14, 2021

(54) METHOD FOR PREPARING PRIMARY DIAMINES BY KOLBE ELECTROLYSIS COUPLING REACTION

(71) Applicants: RHODIA OPERATIONS, Aubervilliers (FR); BASF FRANCE SAS, Levallois-Perret (FR)

(72) Inventors: Mengjia Wu, Shanghai (CN); Stéphane Streiff, Shanghai (CN); Sergio Mastroianni, Lyons (FR)

(73) Assignees: RHODIA OPERATIONS, Aubervilliers (FR); BASF FRANCE SAS, Levallois-Perret (FR)

( * ) Notice: Subject to any disclaimer, the term of this patent is extended or adjusted under 35 U.S.C. 154(b) by 0 days.

(21) Appl. No.: 16/772,628

(22) PCT Filed: Dec. 21, 2017

(86) PCT No.: PCT/CN2017/117626
§ 371 (c)(1),
(2) Date: Jun. 12, 2020

(87) PCT Pub. No.: WO2019/119337
PCT Pub. Date: Jun. 27, 2019

(65) Prior Publication Data
US 2020/0385333 A1 Dec. 10, 2020

(51) Int. Cl.
*C07C 209/68* (2006.01)
*C07C 211/12* (2006.01)
*C25B 3/29* (2021.01)

(52) U.S. Cl.
CPC .......... *C07C 209/68* (2013.01); *C07C 211/12* (2013.01); *C25B 3/29* (2021.01)

(58) Field of Classification Search
None
See application file for complete search history.

(56) References Cited

PUBLICATIONS

Weiper-Idelmann et al. (Acta Chemica Scandinavica, 1998, 52, 672). (Year: 1998).*

* cited by examiner

*Primary Examiner* — Sudhakar Katakam
*Assistant Examiner* — Jennifer C Sawyer

(57) ABSTRACT

The present invention relates to a method for preparing primary diamines from amino acid compounds. Specifically, this invention is related to the preparation of a primary diamine from an amino acid and/or its salt by Kolbe electrolysis coupling reaction.

17 Claims, 1 Drawing Sheet

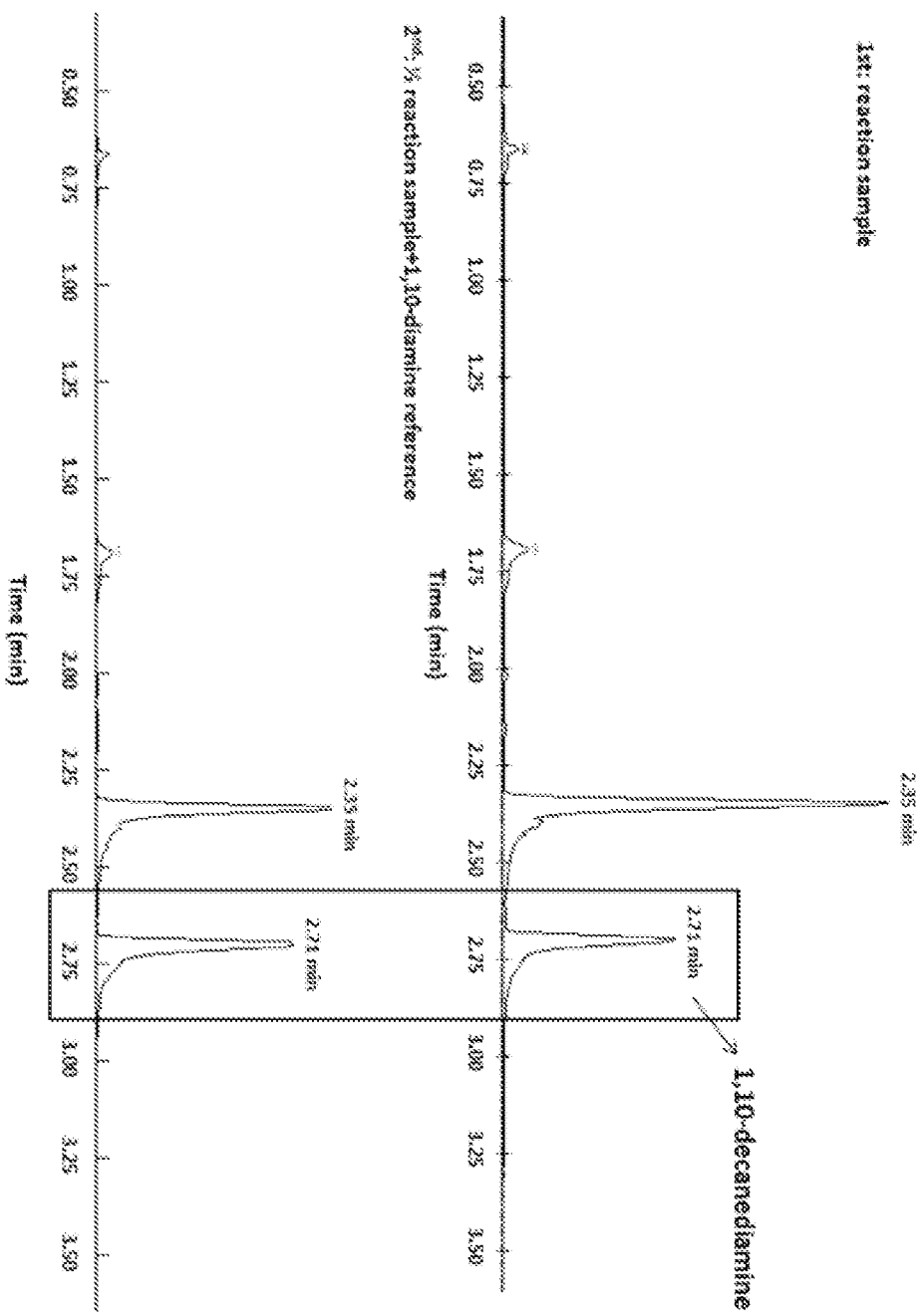

METHOD FOR PREPARING PRIMARY DIAMINES BY KOLBE ELECTROLYSIS COUPLING REACTION

This application is a U.S. national stage entry under 35 U.S.C. § 371 of International Application No. PCT/CN2017/117626, filed on Dec. 21, 2017. The entire contents of this application is explicitly incorporated herein by this reference.

TECHNICAL FIELD

The present invention relates to a method for preparing primary diamines from amino acid compounds. Specifically, this invention is related to the preparation of a primary diamine from an amino acid and/or its salt by Kolbe electrolysis coupling reaction.

BACKGROUD

Aliphatic amines are of considerable industrial importance and find applications in almost every field of modern technology such as chemistry, agriculture, and pharmaceutical. Especially, aliphatic diamines are valuable intermediates in organic syntheses. Certain aliphatic diamines, for example, linear aliphatic diamines are particularly useful as monomer raw materials in the synthesis of polyamide and polyurethane resin, and as intermediates for pharmaceutical and agrochemical raw material.

It is known that aliphatic monoamines can be prepared by condensing monohydric alcohols with ammonia in the presence of a metallic hydrogenation catalyst. Similarly, aliphatic diamines can be prepared by condensing dihydric alcohols with ammonia in the presence of a hydrogenation catalyst. Thus, the desirability of producing diamines by amination of the corresponding diols has been seriously limited due to use of hydrogenation catalyst in the manufacture process. In view of all the above, there is still a very strong need in the art to develop an improved process of manufacturing primary diamines without using of hydrogenation catalyst.

The Kolbe electrolysis coupling reaction is one of the oldest and well-known electro-organic reaction and is defined as one-electron oxidation of carboxylate ion RCOO— with decarboxylation that leads to a radical R. These radicals can dimerize to form a larger molecule R-R via Kolbe electrolysis coupling reaction. The overall reaction is summarized by Scheme 1:

Scheme 1

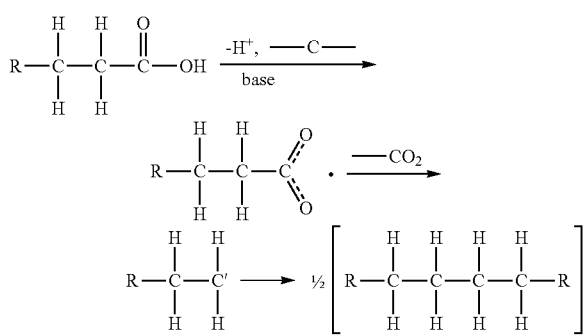

Weiper-Idelmann et al, *Acta Chemica Scandinavica* 52 (1998) pp. 672-682 reports dimerization of fatty acids having long chain hydrocarbons by Kolbe electrolysis coupling reaction. U.S. Pat. No. 7,582,777 describes a method for producing a long chain ($C_{22}$-$C_{50}$) polyunsaturated hydrocarbon via Kolbe electro-coupling of $C_{12}$-$C_{26}$ fatty acids.

Haufe, J. et al, *Chemie Ingenieur Technik*, 1970, vol. 42, no. 4, p. 170-175 also reports dimerization of fatty acids derivatives by Kolbe electrolysis coupling reaction as below Scheme 2:

Scheme 2

Wherein X=$C_mH_{2m+1}$, —$C_6H_{2m-1}$, —$C_6H_5$, —$C_5H_4N$, —CO-OAlkyl, —CO—$NH_2$, —CO-Alkyl, —CH(OAlkyl)$_2$, —F, —Cl, —Br, —CN, —NH—CO-R, —NH—$SO_2$-R, —OH, —OAlkyl, —O—OC-Alkyl; n=1, 2, 3 etc. However, when the X is $NH_2$, kolbe electrolysis coupling of amino aliphatic acids to produce primary diamine couldn't be achieved, due to the unprotected amino group is oxidatively attacked during electrolysis reaction, which is demonstrated by the research result of Fichter and Schmidt as early as in 1920 (*Helv. Chim. Acta*, (1920), vol. 3, p. 704). Hans-Jiirgen Schfifer, "Recent Contributions of Kolbe Electrolysis; to Organic Synthesis", *Topics in Current Chemistry*, vol. 152, p. 92-143 also reports that it was unsuccessful to product $NH_2$—$CH_2$—$CH_2$—$NH_2$ from raw material of $NH_2$—$CH_2COOH$ via Kolbe electrolysis coupling reaction.

In view of all the above, there is still a need to provide an improved method for preparing primary diamines, in particular 1,10-decanediamine, which can provide primary diamines in an efficient and simple manner, and thus suitable to be used as a low cost commercial industrial process.

BRIEF DESCRIPTION OF DRAWINGS

FIG. 1 Liquid chromatography spectroscopies demonstrate that 1,10-decanediamine is synthesized during Kolbe electrolysis coupling reaction according to the Example 1 of this invention.

Definitions

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The term "and/or" includes the meanings "and", "or" and also all the other possible combinations of the elements connected to this term.

Throughout the description, including the claims, the term "comprising one" should be understood as being synonymous with the term "comprising at least one", unless otherwise specified, and "between" should be understood as being inclusive of the limits.

It should be noted that in specifying any range of concentration, any particular upper concentration can be associated with any particular lower concentration.

It is specified that, in the continuation of the description, unless otherwise indicated, the values at the limits are included in the ranges of values which are given.

As used herein, the term "amino acids" are organic compounds containing amine (—NH$_2$) and carboxyl (—COOH) functional groups, along with a side chain (R group) specific to each amino acid.

As used herein, an "anode" is an electrode through which conventional current flows into a polarized electrical device.

As used herein, a "cathode" is the electrode from which a conventional current leaves a polarized electrical device.

As used herein, the term "hydrocarbon group" refers to a group which contains carbon and hydrogen bonds. A hydrocarbon group may be linear, branched, or cyclic, and may contain a heteroatom such as oxygen, nitrogen, sulfur, halogen, etc.

As used herein, the term "alkyl" means a saturated hydrocarbon radical, which may be straight, branched or cyclic, such as, methyl, ethyl, n-propyl, iso-propyl, n-butyl, sec-butyl, t-butyl, pentyl, n-hexyl, cyclohexyl.

As used herein, the term "alkenyl" as a group or part of a group denotes an aliphatic hydrocarbon group containing at least one carbon-carbon double bond and which may be straight or branched. The group may contain a plurality of double bonds in the normal chain and the orientation about each is independently E or Z. Exemplary alkenyl groups include, but are not limited to, ethenyl, propenyl, butenyl, pentenyl, hexenyl, heptenyl, octenyl and nonenyl. The group may be a terminal group or a bridging group.

As used herein, the term "aryl" refers to a monovalent aromatic hydrocarbon group, including bridged ring and/or fused ring systems, containing at least one aromatic ring. Examples of aryl groups include phenyl, naphthyl and the like. The term "arylalkyl" or the term "aralkyl" refers to alkyl substituted with an aryl. The term "arylalkoxy" refers to an alkoxy substituted with aryl.

As used herein, the term "cyclic group" means a closed ring hydrocarbon group that is classified as an alicyclic group, aromatic group, or heterocyclic group.

The term "alicyclic group" means a cyclic hydrocarbon group having properties resembling those of aliphatic groups.

As used herein, the term "cycloalkyl" as used herein means cycloalkyl groups containing from 3 to 8 carbon atoms, such as for example cyclohexyl.

The heterocyclic group may also mean a heterocyclic group fused with a benzene-ring wherein the fused rings contain carbon atoms together with 1 or 2 heteroatom's which are selected from N, O and S.

As used herein, the term "heterocycloalkane" means a saturated heterocycle formally derived from a cycloalkane by replacing one or more carbon atoms with a heteroatom.

As used herein, the terminology "(C$_n$-C$_m$)" in reference to an organic group, wherein n and m are each integers, indicates that the group may contain from n carbon atoms to m carbon atoms per group.

DETAILED DESCRIPTION

Through continuous studies concerning improved method for preparing primary diamines which overcome the above-mentioned problems in the art, the applicant has now surprisingly found that it is possible to advantageously prepare primary diamines by using amino acid compounds as the raw materials through Kolbe electrolysis coupling reaction by control of current density and water content in the reaction medium, and proper choice of solvents, electrolytes. The present invention can overcome all the drawbacks of prior art processes.

It is a promising way to realize industrialization since the reaction equipment according to the present invention is simple. It is also possible to avoid the hydrogenation catalyst in the reaction medium. Furthermore, the step of protecting the amino group is not necessary for the invented method.

It is an object of this invention to provide an improved method for preparing a primary diamine of the general formula (II) [Compound (II), hereinafter] from an amino acid compound of the general formula (I) [Compound (I), hereinafter]

$$H_2N\text{-}T\text{-}COOX \qquad (I)$$

$$H_2N\text{-}T\text{-}T\text{-}NH_2 \qquad (II)$$

by a Kolbe electrolysis coupling reaction in a reaction medium comprising:
a solvent,
an electrolyte, and
the amino acid compound of the general formula (I), wherein
T represents a linear or branched C$_1$-C$_{10}$ alkylene group,
X represents H$^+$ or alkali metal cation,
the reaction is performed under a current density of less than 400 mA/cm$^2$.

Without wishing to be bound by any theory, the Kolbe electrolysis coupling reaction according to the present invention can successfully convert compound (I) to compound (II) by a one-step reaction.

In a preferred embodiment, the reaction medium can be free or substantially free of water.

As used herein, the term "substantially free" means when some amount of water is present in the reaction medium, this amount does not affect significantly the conversion of the Compound (I) into the Compound (II) (a Student's t-test, e.g. with a p-value cut-off arbitrarily set at alpha=0.05, could be used to determine whether the conversion obtained in the presence of this amount of water differs significantly, from a statistical standpoint, from the conversion in the total absence of water). Accordingly, in some embodiments, in particular when the electrolyte is an alkoxide, the reaction medium comprises advantageously less than 0.01% wt of water, based on the total weight of the reaction medium, notably at the beginning of the reaction; and preferably during the reaction.

As used herein, the term "completely free" when used with reference to the absence of water in the medium of the present invention, means that the reaction comprises no water at all.

Preferably, T may preferably represent a linear or branched C$_1$-C$_6$ alkylene group.

Preferably, X may preferably represent sodium cation or potassium cation.

Preferred Compound (II) according to the present can be selected from a group consisting of 1,10-decanediamine, 1,8-octanediamine, 1,6-hexanediamine, 1,4-butanediamine and 1,2-ethylenediamine. More preferred Compound (II) is 1,10-decanediamine.

The Compound (I) can be the amino acid or its corresponding alkali metal salts. It should be understood the Compound (I) can also be a mixture of the amino acid and its corresponding alkali metal salts.

Preferred Compound (I) can be selected from a group consisting of 6-aminohexanoic acid, 5-aminopentanoic acid, 4-aminobutanoic acid, 3-aminopropanoic acid and aminoacetic acid. More preferred Compound (I) is 6-aminohexanoic acid.

Preferred reactions according to the present invention are the following:
Preparation of 1,2-ethylenediamine from aminoacetic acid;
Preparation of 1,4-butanediamine from 3-aminopropanoic acid;
Preparation of 1,6-hexanediamine from 4-aminobutanoic acid;
Preparation of 1,8-octanediamine from 5-aminopentanoic acid;
Preparation of 1,10-decanediamine from 6-aminohexanoic acid.

The Compound (I) can notably be obtained from hydrolysis of lactam under alkaline or acidic conditions. For example, 6-aminohexanoic acid or salt can be obtained from hydrolysis of caprolactam under alkaline or acidic conditions as illustrated by Scheme 3 and Scheme 4.

Scheme 3

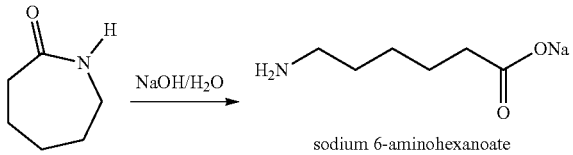

sodium 6-aminohexanoate

Scheme 4

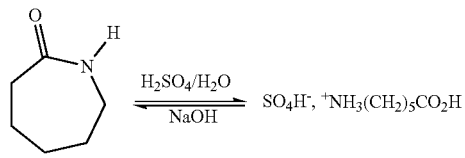

Example of the lactams can be substituted or unsubstituted ε-Lactam, substituted or unsubstituted δ-Lactam, substituted or unsubstituted γ-Lactam, substituted or unsubstituted β-Lactam, substituted or unsubstituted α-Lactam, preferably selected from a group consisting of unsubstituted ε-Lactam, unsubstituted δ-Lactam, unsubstituted γ-Lactam, unsubstituted β-Lactam or unsubstituted α-Lactam. Most preferred lactam is ε-Lactam (caprolactam).

Thus, the method may further comprise the following steps before the Kolbe electrolysis coupling reaction:
(a) hydrolyzing a lactam to provide the Compound (I),
(b) optionally dehydrating the Compound (I) obtained at step (a).

The concentration of the Compound(I) in the reaction medium is from 0.05 to 2 mol/L, preferably from 0.1 to 0.6 mol/L.

The solvent for the Kolbe electrolysis coupling reaction of the present invention can be selected from, for example, methanol, ethanol, propanol, acetone, acetonitrile, THF (tetrahydrofuran), DMF (N,N-dimethylformamide), DMSO (dimethylsulfoxide), NMP (N-Methyl-2-pyrrolidone), DMC (dimethyl carbonate), NM (nitromethane), PC (propylene carbonate), EC (ethylene carbonate), toluene, xylene, dimethylformamide, hexane, pentane, heptane, octane, nonane, decane, undecane, dodecane and ionic liquids. Said ionic liquid may be alkylammonium salt such as tetraalkylammonium halides, tetraalkylammonium perchlorates, tetraalkylammonium tetrafluoroborates.

It should be understood that the solvent mentioned above could be used independently or in the form of mixtures.

The solvent is preferably alcohol, such as methanol or ethanol.

It can be understood by a skilled person in the art that an electrolyte is a chemical compound, which is easy to be dissolved into the solvent and does not interfere with the electrochemical reactions. Inorganic compounds used as electrolyte can be alkali metal salt or alkaline earth metal salt. Organic compounds used as electrolyte can be methoxide and ethoxide, or ionic liquids, especially alkylammonium salt such as tetraalkylammonium halides, tetraalkylammonium perchlorates, tetraalkylammonium tetrafluoroborates.

Examples of inorganic compound used as electrolyte notably are:
Halides, such as lithium chloride, sodium chloride, potassium chloride, lithium bromide, sodium bromide and potassium bromide, magnesium chloride, magnesium bromide.
Nitrates, such as lithium nitrate, sodium nitrate, potassium nitrate, magnesium nitrate.
Perchlorates, such as lithium perchlorate, sodium perchlorate, potassium perchlorate, magnesium perchlorate.

Examples of organic compound used as electrolyte notably are:
Methoxide and ethoxide
Tetraalkylammonium halides, such as tetrabutyl ammonium bromide, tetrabutyl ammonium chloride, tetraoctyl ammonium bromide, tetraoctyl ammonium chloride.

Preferably, the electrolyte can notably be a base electrolyte and more preferably an alkoxide selected from a group consisting of sodium methoxide, potassium methoxide, sodium ethoxide and potassium ethoxide.

In a preferred embodiment, the reaction medium may comprise methanol, sodium methoxide and the amino acid compound of the general formula (I).

The molar ratio of the Compound (I) to the electrolyte can be in a range of 2:1 to 1:5, preferably 1:2 to 1:4. More preferably, the rang can be equal to 1:2.5, 1:2.6, 1:2.7, 1:2.8, 1:2.9, 1:3.0, 1:3.1, 1:3.2, 1:3.3, 1:3.4, 1:3.5 or any range obtained between these values.

The Kolbe electrolysis coupling reaction according to the present invention is under a current density of less than 400 mA/cm$^2$, preferably of less than 200 mA/cm$^2$ and more preferably of less than 100 mA/cm$^2$. At the same time, the process according to the present invention is preferably carried out under a current density of at least 20 mA/cm$^2$, preferably of at least 30 mA/cm$^2$ and more preferably of at least 50 mA/cm$^2$.

In a preferred embodiment, the current density is from 100 to 200 mA/cm$^2$.

It can be understood by a skilled person in the art that at least one anode and one cathode are immersed in the reaction medium. The current density and potential between the anode and the cathode could be controlled by a potentiostat/galvanostat device or any direct current (DC) power supply unit.

The anode and cathode are selected among conductive materials, such as noble metals, transition metals, metal alloys, and carbon. Specifically, the anode could be selected from platinum, platinum-plated titanium, iridium, gold, palladium, lead dioxide, glassy carbon or carbon electrodes. It is preferable to use platinum, platinum-plated titanium and glassy carbon as anode. The cathode provides a passage for current flow, therefore a material with good conductivity is preferred. Such cathode could be selected among platinum, gold, palladium, carbon.

Conventional reference electrode, such as saturated calomel electrode, Ag/AgCl electrode, Ag ion electrode, solid Pt electrode can be optionally used in the present invention when potentiostat/galvanostat device is used.

Electrodes described above may be directly used as an bulk electrode in different shapes, such as sheet, plate, foil, cylinder, belt, disk, net, foam or any other shapes, which could be manufactured by skilled people in the field. The electrode can also be manufactured to be porous or hierarchical to increase the surface area.

The applied potential between anode and cathode can be controlled to avoid decomposition or polymerization of primary diamines. Said potential is between 1-15 V, and preferably below or equal to 12 V.

The Kolbe reaction can be carried out either in batch or continuous mode. When carrying out in a continuous mode, the reaction mixture is continuously flow through a pair of electrode with narrow gap (<1 mm), which is held at desired voltage to maintain current flow. To scale up the process, a series of the narrow gap electrochemical reactors (cells) can be stacked either in parallel or in series. The reservoir containing the reaction mixture optionally can be heated at a desired temperature, 20-50° C. to maintain the solubility.

The reaction temperature according to the present invention are from 20-50° C., preferably at room temperature. When electrolysis volume increases, the temperature of the electrolysis solution rises, so it is preferable to maintain the temperature by soaking the electrolytic cell in water bath. Also, it is preferable to stir the electrolyte solution in order to maintain a uniform temperature.

The Kolbe electrolysis coupling reaction time according to the present invention is from 0.5 to 36 hours, preferably from 1 to 10 hours, more preferably between 2 to 6 hours.

The Kolbe electrolysis coupling reaction according to the present invention is advantageously pursued while taking care to avoid the presence of any reactive gases in the electrolytic cell. These reactive gases may be notably oxygen, water and carbon dioxide. $O_2$ and water are the most reactive and should therefore be avoided. The reactants, solvents and electrolytes may advantageously be anhydrous.

The invention also concerns a composition comprising:
a solvent,
an electrolyte, and
an amino acid compound of the general formula (I) and/or a primary diamine of the general formula (II)

$H_2N$-T-COOX         (I)

$H_2N$-T-T-$NH_2$         (II)

Preferably, the composition comprising:
a solvent,
an electrolyte, and
an amino acid compound of the general formula (I).

Advantageously, the composition mentioned above can be free or substantially free of water.

The invention also concerns a primary diamine susceptible of being obtained by the process.

The following examples are included to illustrate embodiments of the invention. Needless to say, the invention is not limited to the described examples.

Experimental Part

Raw Materials 1,10-decanediamine (purity>97%) was procured from J&K 6-aminohexanoic acid (abbreviation as ACA, 99%) was procured from J&k Sodium methoxide (abbreviation as MeONa, anhydrous, 99%) was procured from J&K Methanol, hydrous, HPLC garde, (purity>99.9%) was procured from Merck $H_2SO_4$, (purity>95%) was procured from Sinopharm NaOH, (purity>96%) was procured from Sinopharm Example 1

Before electrolysis, the electrolysis solution was degassed by Ar to remove $O_2$ and $CO_2$ to avoid the reaction of $O_2$ with the radicals formed in the reaction. On the other hand, this step can be used to avoid the reaction of $CO_2$ with hydroxide to form insoluble carbonates in methanol solution. All the raw materials should be anhydrous.

In a cylindrical glass container with a capacity of 100 ml, 1.97 g of 6-aminohexanoic acid 15 mmol) is dissolved in 100 ml of methanol, and 1.62 g of sodium methoxide (30 mmol) is added as a supporting electrolyte. Platinum anode (platinum foil of 1*2 $cm^2$) and platinum cathode (Pt net of 2*2 $cm^2$) are provided with 10 mm distances between the two electrodes, and constant current controlled electrolysis is carried out at 200 mA/$cm^2$. During the experiment, an upper limit of potential was set at 12 V. At the time as the electrolysis, large amounts of bubbles were generated, and rising of electrolysis solution temperature was observed. In order to maintain electrolysis solution to approximately the same temperature, it is preferable to soaking the electrolytic cell in water bath, and maintains electrolysis temperature at room temperature. The reaction was conducted at room temperature for 4 hrs with continuous stirring non-aqueous electrolyte at 180 rpm.

The reaction product is analyzed by high performance liquid chromatography. UPLC-MS (Waters Acquity H-Class with SQD2) was used for the analysis of reaction product. 1,10-decanediamine and 6-aminohexanoic acid were diluted into eluent (Acetonitrile: $H_2O$=90:10) with concentrations ranging from 0.1-2 ppm and 0.2-10 ppm as reference samples, respectively.

Two samples were prepared for high performance liquid chromatography analysis. Sample 1 was obtained by using Acetonitrile: $H_2O$=90:10 as eluent to dilute 20 times of reaction product after Kolbe electrolysis coupling reaction in accordance with Example 1 of the invention, and then filtered with organic filter of 0.22 μm to remove precipitates. Sample 2 was obtained by using Acetonitrile: $H_2O$=90:10 as eluent to dilute 40 times of reaction product obtained after Kolbe electrolysis coupling reaction in accordance with Example 1 with addition of above 1,10-decanediamine reference sample. The liquid chromatography spectroscopies of samples 1 and 2 are illustrated in FIG. 1.

As can be seen from the LC spectroscopies of the mentioned 2 samples, the peak position at RT=2.71 min, which represents of the desired product, i.e. 1,10-decanediamine, keeps the same in sample 1 and 2. Meanwhile the peak intensity at RT=2.71 min of the sample 2 is doubled after introducing 1,10-decanediamine. On the other hand, the byproduct peak at RT=2.35 min reduces by 50% after addition of 1,10-decanediamine. All these results demonstrated that the 1,10-decanediamine is synthesized during Kolbe electrolysis coupling reaction according to the Example 1 of this invention.

Examples 2-4

Examples 2-4 are prepared in the same way as example 1, except that different current density is used in the Kolbe coupling reaction as shown in Table 2.

TABLE 2

| Examples | Current density (mA/cm$^2$) | Conversion (%) | Yield (%) |
|---|---|---|---|
| E2 | 50 | 9.0 | 0.41 |
| E3 | 100 | 34 | 1.75 |
| E4 | 150 | 60 | 1.27 |
| E1 | 200 | 72 | 1.20 |

In this example, the impact of current density between anode and cathode was studied, while all the other reaction parameters were kept the same as described in example 1. The reaction products were analyzed by UPLC-MS according to the methodology as described in Example 1. The reaction conversion rate and yield were summarized in Table 2. As shown in Table 2, higher current density could give higher conversion of the reagent 6-aminohexanoic acid, but also lead to more side products. Low current density could give higher selectivity of 1,10-decanediame. But the conversion rate of 6-aminohexanoic acid is low. Base on the above experiment results, the preferably current density is between 100-200 mA/cm$^2$.

Examples 5-6

Examples 5 and 6 are prepared in the same way as example 1, except for the reduced electrode distance (reduced from 10 mm to 4 mm) and reaction time (from 4 hrs to 2 hrs). Higher current densities of 300 and 400 mA/cm$^2$ were studied.

In this example, the impact of current density between anode and cathode was studied at a reduced electrode distance and reaction time compared with examples 1-4. The reaction products were analyzed by UPLC-MS according to the methodology as described in Example 1. The reaction conversion rate and yield were summarized in Table 3.

TABLE 3

| Examples | Current density (mA/cm$^2$) | Conversion (%) | Yield (%) |
|---|---|---|---|
| E5 | 300 | 73 | 0.17 |
| E6 | 400 | 45 | 0.24 |

Examples 7-10

Examples 7-10 are prepared in the same way as example 1, except that different molar concentrations are used for the 6-aminohexanoic acid (ACA) and sodium methoxide (MeONa). According to the examples, the molar ratio between 6-aminohexanoic acid and sodium methoxide was kept at constant as 1:1 and all the other reaction parameters were kept the same as example 1, the impact of the concentration of reagent 6-aminohexanoic acid was studied. The reaction products of these examples were analyzed by UPLC-MS according to the same methodology as described in Example 1. The reaction conversion rate and yield were summarized in as shown in Table 4.

TABLE 4

| Example | ACA:MeONa | ACA (M) | MeONa (M) | Conversion (%) | Yield (%) |
|---|---|---|---|---|---|
| E7 | 1:1 | 0.15 | 0.15 | 83 | 0.40 |
| E8 | 1:1 | 0.30 | 0.30 | 63 | 0.30 |
| E9 | 1:1 | 0.50 | 0.50 | 68 | 0.38 |
| E10 | 1:1 | 0.60 | 0.60 | 48 | 0.35 |

Example 11

Example 11 are prepared in the same way as example 1, except that other molar ratios between 6-aminohexanoic acid and sodium methoxide are used in the Kolbe electrolysis coupling reaction. According to the example, the impact of the molar ratio between 6-aminohexanoic acid and sodium methoxide (1:1, 1:2 and 1:3) was studied, while all the other reaction parameters were kept the same as described in example 1. The reaction samples were analyzed by UPLC-MS according to the same methodology as described in Example 1. The corresponding Conversion and yield were also shown in Table 5. As can be seen from Table 5, the optimized ratio of ACA to MeONa is 1:3.

TABLE 5

| Example | ACA:MeONa | ACA (M) | MeONa (M) | Conversion (%) | Yield (%) |
|---|---|---|---|---|---|
| E7 | 1:1 | 0.15 | 0.15 | 83 | 0.40 |
| E1 | 1:2 | 0.15 | 0.30 | 72 | 1.20 |
| E11 | 1:3 | 0.15 | 0.45 | 76 | 1.82 |

The invention claimed is:

1. A method for preparing a primary diamine of the general formula (II) from an amino acid compound of the general formula (I)

$$H_2N\text{-}T\text{-}COOX \quad (I)$$

$$H_2N\text{-}T\text{-}T\text{-}NH_2 \quad (II)$$

by a Kolbe electrolysis coupling reaction in a reaction medium comprising:
 a solvent,
 an electrolyte, and
 the amino acid compound of the general formula (I),
wherein
 T represents a linear or branched C1-C$_{10}$ alkylene group,
 X represents H$^+$ or alkali metal cation,
 the reaction is performed under a current density of less than 400 mA/cm$^2$.

2. The method according to claim 1, wherein T represents a linear or branched C$_1$-C$_6$ alkylene group.

3. The method according to claim 1, wherein the primary diamine is selected from the group consisting of 1,10-decanediamine, 1,8-octanediamine, 1,6-hexanediamine, 1,4-butanediamine and 1,2-ethylenediamine.

4. The method according to claim 1, wherein the amino acid compound is selected from the group consisting of 6-aminohexanoic acid, 5-aminopentanoic acid, 4-aminobutanoic acid, 3-aminopropanoic acid and aminoacetic acid.

5. The method according to claim 1, wherein the concentration of the amino acid compound in the reaction medium is from 0.05 to 2 mol/L.

6. The method according to claim 1, wherein the solvent is selected from the group consisting of methanol, ethanol, propanol, acetone, acetonitrile, THF (tetrahydrofuran), DMF (N,N-dimethylformamide), DMSO (dimethylsulfoxide), NMP (N-Methyl-2-pyrrolidone), DMC (dimethyl carbonate), NM (nitromethane), PC (propylene carbonate), EC (ethylene carbonate), toluene, xylene, dimethylformamide, hexane, pentane, heptane, octane, nonane, decane, undecane, dodecane and ionic liquids.

7. The method according to claim 6, wherein the solvent is methanol or ethanol.

8. The method according to claim 1, wherein the electrolyte is a base electrolyte.

9. The method according to claim 8, wherein the electrolyte is an alkoxide.

10. The method according to claim 9, wherein the electrolyte is selected from the group consisting of sodium methoxide, potassium methoxide, sodium ethoxide and potassium ethoxide.

11. The method according to claim 1, wherein the reaction medium is free or substantially free of water.

12. The method according to claim 1, wherein the molar ratio of the amino acid compound to the electrolyte is in a range of 2:1 to 1:5.

13. The method according to claim 1, wherein the Kolbe electrolysis coupling is carried out under direct current.

14. The method according to claim 1, wherein the current density is from 100 to 200 mA/cm$^2$.

15. The method according to claim 1, wherein the reaction time is from 2 to 6 hours.

16. The method according to claim 1, wherein the reaction temperature is from 20-50° C.

17. The method according to claim 1, wherein the method further comprises the following steps before the Kolbe electrolysis coupling reaction:
(a) hydrolyzing of a lactam to provide the Compound (I),
(b) optionally dehydrating the Compound (I) obtained at step (a).

* * * * *